(12) United States Patent
De Lange et al.

(10) Patent No.: US 8,263,784 B2
(45) Date of Patent: Sep. 11, 2012

(54) METHOD FOR THE SYNTHESIS OF A RAMIPRIL INTERMEDIATE

(75) Inventors: Ben De Lange, Munstergeleen (NL); Dennis Heemskerk, Schinveld (NL)

(73) Assignee: DSM Sinochem Pharmaceuticals Netherlands B.V., Delft (NL)

( * ) Notice: Subject to any disclaimer, the term of this patent is extended or adjusted under 35 U.S.C. 154(b) by 0 days.

(21) Appl. No.: 13/126,871

(22) PCT Filed: Oct. 27, 2009

(86) PCT No.: PCT/EP2009/064103
§ 371 (c)(1),
(2), (4) Date: Apr. 29, 2011

(87) PCT Pub. No.: WO2010/049401
PCT Pub. Date: May 6, 2010

(65) Prior Publication Data
US 2011/0263871 A1    Oct. 27, 2011

(30) Foreign Application Priority Data

Oct. 30, 2008   (EP) ..................... 08167945

(51) Int. Cl.
*C07D 209/02*      (2006.01)
(52) U.S. Cl. ........................................ 548/452
(58) Field of Classification Search ............ 548/452
See application file for complete search history.

(56) References Cited

U.S. PATENT DOCUMENTS 5,550,255 A    8/1996   Urbach et al.

FOREIGN PATENT DOCUMENTS

| EP | 0 079 022 | 5/1983 |
| EP | 0 170 775 | 2/1986 |
| WO | WO 2005/049567 | 6/2005 |
| WO | WO 2006/100168 | 9/2006 |

OTHER PUBLICATIONS

International Search Report for PCT/EP2009/064103, mailed Jan. 25, 2010.

*Primary Examiner* — Rebecca Anderson
*Assistant Examiner* — Samantha Shterengarts
(74) *Attorney, Agent, or Firm* — Nixon & Vanderhye P.C.

(57) ABSTRACT

The present invention relates to a process for the preparation of octahydrocyclopenta[b]pyrrole-2-carboxylic acid and esters thereof of general formula (1) in the presence of a cobalt and/or nickel comprising catalyst and to the use of compounds of general formula (1) in the synthesis of ramipril.

(1)

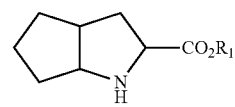

5 Claims, No Drawings

METHOD FOR THE SYNTHESIS OF A RAMIPRIL INTERMEDIATE

This application is the U.S. national phase of International Application No. PCT/EP2009/064103 filed 27 Oct. 2009 which designated the U.S. and claims priority to EP 08167945.8 filed 30 Oct. 2008, the entire contents of each of which are hereby incorporated by reference.

FIELD OF THE INVENTION

The present invention relates to a process for the preparation of octahydrocyclopenta[b]pyrrole-2-carboxylic acid and esters thereof, and to their use in the synthesis of ramipril.

BACKGROUND (2S,3aS,6aS)-octahydrocyclopenta[b]pyrrole-2-carboxylic acid and esters thereof of formula (1),

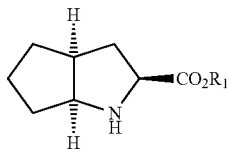
(1)

wherein $R_1$ represents hydrogen or a carboxyl-protecting group such as benzyl or tert-butyl, are key intermediates for the preparation, as for instance described in EP 79022, of the angiotensin converting enzyme (ACE) inhibitor ramipril ([2S,3aS,6aS]-1-[(2S)-2-[[(1S)-1-(ethoxycarbonyl)-3-phenylpropyl]-amino]-1-oxopropyl]octahydrocyclopenta-[b]-pyrrole-2-carboxylic acid) of formula (2).

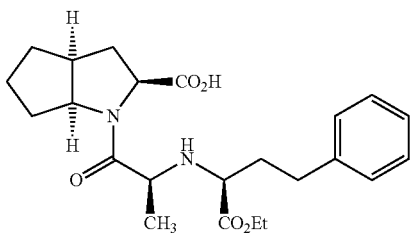
(2)

The preparation of compounds of general formula (1) is known from various documents such as EP 79022, EP 170775, EP 1692106, EP 190224 and WO 2006/100168 and several of these approaches rely on introduction of the required chirality by hydrogenation catalyzed by high molecular weight transition state metals such as palladium, platinum and rhodium. The species that undergoes hydrogenation is a species of general formula (3).

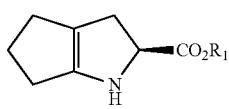
(3)

A major drawback of the use of high molecular weight transition state metals in hydrogenation reactions is the fact that these metals are rare, expensive, highly poisonous and require dedicated recycling procedures that are economically unattractive as they usually are carried out on a relatively small scale. However, all prior art points to the belief that only high molecular weight transition state metals can afford the required degree of stereoselectivity.

DETAILED DESCRIPTION OF THE INVENTION

In a first aspect of the present invention a method is disclosed for the preparation of a compound of general formula (1),

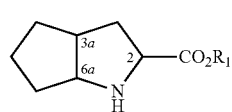
(1)

wherein $R_1$ is hydrogen or a carboxylic acid protecting group, comprising hydrogenation of a compound of general formula (3),

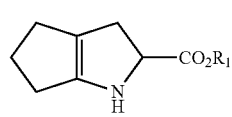
(3)

wherein $R_1$ is as defined above for compound (1), in the presence of a catalyst characterized in that said catalyst comprises cobalt and/or nickel. Surprisingly it was found that cobalt- and nickel-containing hydrogenation catalysts, such as for instance so-called sponge-metal catalysts like Raney-cobalt or Raney-nickel or the sponge-metal catalysts described in WO 2004/091777, perform in the method of the present invention equally well or even better than high molecular weight transition state metals such as palladium and platinum. The use of nickel has been mentioned in U.S. Pat. No. 7,157,484, however this document deals with the synthesis of perindopril and not ramipril. As the perindopril intermediate in question is a bicyclic system comprising of a five- and a six-membered ring whereas for ramipril these are two five-membered rings, the marked difference in ring-constraint makes it impossible to expect success in one case if it was established in the other case. However, U.S. Pat. No. 7,157,484 gives no indication about possible success as the experimental data are based on a platinum-containing catalyst only. In contrast, cobalt- or nickel-containing sponge-metal catalysts are known for their ability to effect racemization as described for instance by Parvulescu et al. (Adv. Synth. Cat. (2008) 350, 113-121). Other suitable cobalt- and/or nickel-containing catalysts are those based on precipitation of the metal on silica as described in U.S. Pat. No. 4,014,819, bimetallic cobalt-nickel powder catalysts, but also cobalt- and/or nickel containing catalysts promoted by small amounts of ruthenium, such as described in U.S. Pat. No. 4,855,505.

In a first embodiment, the method of the present invention comprises dissolving or suspending the appropriate starting material, for example a compound of general formula (3) or a precursor thereof in a solvent. Suitable solvents are water, alcohols such as methanol, ethanol, n-propanol, iso-propanol but are not limited to these examples. The mixture so obtained is then treated under hydrogen-pressure, preferably ranging from 1 to 100 bar, more preferably from 2 to 50 bar, most preferably from 5 to 25 bar, with one or more of the cobalt- or nickel-comprising catalysts described above. The amount of cobalt- or nickel-comprising catalyst may range from 0.1 to 1000 g/mol substrate, preferably from 1 to 100 g/mol substrate, more preferably from 3 to 75 g/mol substrate, most preferably from 5 to 50 g/mol substrate. Preferably pH-values at which the method of the present invention can be carried out optimally are those ranging from 1 to 9, more preferably ranging from 2 to 8, most preferably ranging from 3 to 7, still most preferably ranging from 4 to 6. Suitable reaction temperatures are from 0 to 100° C., preferably from 10 to 95° C., more preferably from 20 to 90° C., most preferably from 30 to 85° C., still most preferably from 40 to 80° C. Suitable reaction times are from 1 to 48 h, preferably from 2 to 24 h, more preferably from 4 to 20 h, most preferably from 10 to 18 h. After the reaction is completed or partially completed under the conditions outlined above, the catalyst is removed by techniques known to the skilled person, such as centrifugation, filtration, precipitation and the like and the product can be isolated from the resulting solution or suspension by chromatography, crystallization, precipitation, evaporation, freeze-drying and the like.

In a second embodiment, the group $R_1$ in compounds (1) and (3) is alkenyl or substituted alkenyl, alkyl or substituted alkyl, alkylcarbonyl or substituted alkylcarbonyl, aryl or substituted aryl, arylcarbonyl or substituted arylcarbonyl, silyl or substituted silyl, sulfonyl or substituted sulfonyl. Preferred groups $R_1$ are 9-anthrylmethyl, benzyloxymethyl, p-bromobenzyl, p-bromophenacyl, 3-buten-1-yl, t-butyldimethylsilyl, di-t-butylmethylsilyl, t-butyldiphenylsilyl cyclohexyl, carboxamidomethyl, ω-chloroalkyl, cinnamyl, cyclohexyl, cyclopentyl, cyclopropylmethyl, 5-dibenzosuberyl, 2,6-dichloro-benzyl, 2,2-dichloro-1,1-difluoroethyl, 2,6-dimethoxybenzyl, 4-(dimethylaminocarbonyl)-benzyl, 2,6-dimethylbenzyl, dimethylthiophosphinyl, 2-(9,10-dioxo) anthrylmethyl, diphenylmethyl, 2-(diphenylphosphino) ethyl, 1,3-dithianyl-2-methyl, 9-fluorenylmethyl, 2-haloethyl, hydrogen, isopropyldimethylsilyl, p-methoxybenzyl, methoxyethoxymethyl, methoxymethyl, p-methoxyphenacyl, α-methylcinnamyl, p-(methylmercapto)phenyl, α-methylphenacyl, 1-methyl-1-phenylethyl, 4-(methylsulfinyl)benzyl, o-nitrobenzyl, p-nitrobenzyl, bis(o-nitrophenyl) methyl, 2-(p-nitrophenylsulfenyl)ethyl), n-pentyl, phenacyl, phenyldimethylsilyl, N-phthalimidomethyl, 4-picolyl, piperonyl, 1-pyrenylmethyl, 2-(2'-pyridyl)ethyl, 4-sulfobenzyl, 2-tetrahydrofuranyl, 2-tetrahydropyranyl, 2-(p-toluene-sulfonyl)ethyl, 2,2,2-trichloroethyl, triethylsilyl, 2-(trifluoromethyl)-6-chromylmethyl, 2,4,6-trimethylbenzyl, 4-(trimethylsilyl)-2-buten-1-yl, 2-(trimethylsilyl)ethyl, 2-(trimethylsilyl)ethoxymethyl and triphenylmethyl. Most preferred groups are those that are relatively cheap and have a relative low molecular weight such as allyl, benzyl, n-butyl, sec-butyl, t-butyl, 1,1-dimethylpropyl, 1,2-dimethylpropyl, 2,2-dimethylpropyl, ethyl, isobutyl, isopropyl, methyl, 1-methylbutyl, 2-methylbutyl, 3-methylbutyl, methyl carbonyl, methylthiomethyl, 2-methylthioethyl, phenyl, propyl and trimethylsilyl.

Compound (3) can be used as starting material but in a third embodiment compounds of general formula (3) can also be formed in situ from various synthetic approaches, an example of which is described in WO 2008/067981. Hence, in another embodiment, the method of the present invention also comprises hydrogenation in the presence of a catalyst comprising cobalt or nickel of compounds that will form compound (3) in situ an example of which are those of general formula (4a) or (4b),

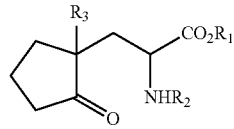

(4a)

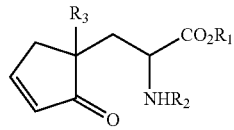

(4b)

wherein $R_1$ is as defined above for compound (1), $R_2$ is alkyl, aryl, carbamoyl or hydrogen and $R_3$ is optionally protected carboxyl or hydrogen. $R_1$ and $R_2$ can also be connected forming a cyclic structure such as a hydantoin. Preferably such compounds of general formula (4a) or (4b) have the S-configuration (this is the L-configuration) for at least 95% as this is the configuration required for ramipril. More preferably they have the S-configuration for at least 98%, most preferably for at least 99%.

In a second aspect of the invention, the products of the method of the first aspect are used in the preparation of ramipril.

In one embodiment, (2S,3S,6S)-octahydrocyclopenta[b] pyrrole-2-carboxylic acid ([1], $R_1$=H) is coupled with a compound of general formula [5],

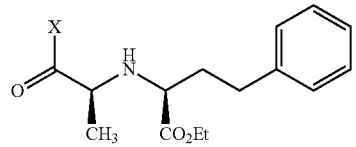

(5)

wherein X is halogen or $OC(O)R_4$ with $R_4$ being alkyl or aryl to give ramipril. In the present invention it was found that coupling of the free acid (2S,3S,6S)-octahydrocyclopenta[b] pyrrole-2-carboxylic acid ([1], R=H) with a suitably activated derivative of compound [5] or a salt thereof yielded ramipril in excellent yield and purity. It was thus surprisingly established that compounds [5] or their salts could be coupled directly with compound [1] (R=H) without any secondary amine protection.

Suitably activated derivatives of compound [5] include halogenides, i.e. wherein X is halogen such as bromine, chlorine, fluorine or iodine. Preferred compounds are [5] with X is bromine and [5] with X is chlorine; also mixtures can be used. Said halogenides can be prepared from compound [5] with X is OH using methods that are known to the skilled person. Other suitably activated derivatives of compound [5] are those wherein X is $OC(O)R_4$ with $R_4$ being alkyl, aryl and the like.

In one embodiment (2S,3S,6S)-octahydrocyclopenta[b] pyrrole-2-carboxylic acid ([1], R=H) is first treated with a base, for instance an alkali alkoxide such as potassium ethoxide, potassium methoxide, sodium ethoxide or sodium methoxide. Preferably the coupling reaction with [5] is carried out also in the presence of an organic base such as, for instance, DBN, DBU, diisopropylethylamine, dimethylethylamine, imidazole, triethylamine and the like. In principle the reaction can be carried out at a wide range of temperatures, however in order to avoid unwanted side reactions it is preferred to start at low temperatures, i.e. ranging from −196° C. to 0° C., preferably ranging from −78° C. to −20° C., more preferably ranging from −50° C. to −20° C.

The product obtainable by the use of the second aspect of the present invention is of pharmaceutically acceptable quality or better. The use of the second aspect of the present invention includes the racemic forms as well as the optically pure forms as well as mixtures of the two forms.

EXAMPLES

Example 1

Preparation of 3-(2-oxocyclopentyl)-2-ureidopropanoic acid from methyl 2-acetamido-3-(2-oxocyclopentyl)propanoate

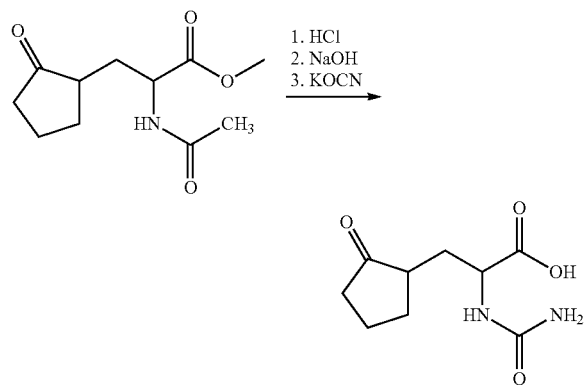

Methyl 2-acetamido-3-(2-oxocyclopentyl)propanoate (52.0 g, 229 mmol, prepared as described in U.S. Pat. No. 5,061,722) was dissolved in 120 mL 6N HCl aq. (720 mmol) and heated at 90-95° C. for 4 h. The resulting reaction mixture was cooled in an ice-bath and neutralized to pH 7.0 with 86 mL 10N NaOH aq. (860 mmol), maintaining the temperature at 15-25° C. Then, potassium cyanate (22.6 g, 278 mmol) was added and the mixture was heated to 60° C. After 3 h, the solution was cooled to 50° C. Decolorizing carbon (3.0 g, Norit SX) was added, stirred for 0.5 h and the carbon was filtered off under suction. The remaining solution (pH 8.9) was cooled in an ice-bath and acidified with 6N HCl aq., maintaining the temperature below 10° C. At pH 4.5, the solution was seeded with 0.1 g product. At pH 1.8, the slurry was stirred for 0.5 h and then the product was collected on a filter under suction. The cake was washed with MTBE (2×50 mL) and dried under vacuum. Weight 35.8 g, 73% yield. $^1$H NMR: (DMSO-$d_6$, 300 MHz): δ 12.57 (br s, 1H), 6.22 (dd, 1H), 5.60 (br s, 2H), 4.23-4.04 (m, 1H), 2.27-1.40 (m, 9H).

Example 2

Preparation of 3-(2-oxocyclopentyl)-2-ureidopropanoic acid from propyl 2-acetamido-3-(2-oxocyclopentyl) propanoate

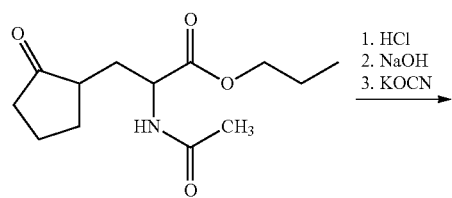

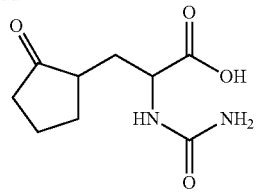

1. Preparation of (R)-propyl 2-acetamido-3-chloropropanoate (S)-Propyl 2-amino-3-hydroxypropanoate HCl salt (18.2 g, 99.1 mmol) was suspended in toluene (96 mL) and then thionyl chloride (8.20 mL, 13.3 g, 112 mmol) was added via an addition funnel during 15 min. The homogeneous reaction was stirred at 20° C. for 2 h. Then, the temperature was raised to 60° C. during 45 min and the reaction was maintained at that temperature for 45 min. Then, acetyl chloride (15.1 mL, 16.7 g, 213 mmol) was added via an addition funnel during a period of 2 h while the temperature reached 80° C. and the reaction was further stirred at that temperature for 30 min. The reaction was allowed to cool to 5° C. while a precipitate formed. The precipitate was collected on a fritted funnel under suction and washed with petroleum benzene (3×25 mL). The cake was dried under vacuum overnight to a final weight of 9.19 g. The mother liquor was seeded with some crystals of the cake and further diluted with petroleum benzene (25 mL) and stirred overnight at 20° C. The ensuing suspension was cooled to 5° C. and the product was collected on a fritted funnel under suction and washed with petroleum benzene (3×25 mL). The cake was dried under vacuum overnight to a final weight of 6.48 g. Combined weight (two cakes) 15.7 g, approx. 76% yield. $^1$H NMR: (CDCl$_3$, 300 MHz): δ 6.40 (br s, 1H), 4.99 (dt, 1H), 4.27-4.11 (m, 2H), 3.95 (dq, 2H), 2.09 (s, 3H), 1.77-1.65 (m, 2H), 0.97 (t, 3H).

2. Preparation of propyl 2-acetamido-3-(2-oxocyclopentyl) propanoate (R)-propyl 2-acetamido-3-chloropropanoate (2.50 g, 12.0 mmol) was dissolved in acetonitrile (25 mL) and 1-pyrrolidino-1-cyclopentene (2.27 mL, 2.14 g, 15.6 mmol) was added. While the reaction was kept at 20° C., dimethylethylamine (1.70 mL, 1.14 g, 15.6 mmol) was added via an addition funnel during 10 min. The homogeneous reaction was stirred at 20° C. for 21 h. Then, water (0.50 mL) was added and the reaction was further stirred for 2.5 h. The solvents were removed in vacuo at 50° C. and the residual oil was purified by silica gel flash chromatography using an EtOAc: petroleum benzene gradient. The product is a yellowish oil. Weight 2.67 g, approx. 87% yield (two diastereomers). $^1$H NMR: (CDCl$_3$, 300 MHz): δ 6.62 (br d, 0.5H), 6.38 (br d, 0.5H), 4.61-4.49 (m, 1H), 4.05-4.00 (m, 2H), 2.38-1.92 (m, 8H), 1.80-1.47 (m, 6H), 0.90-0.84 (m, 3H).

3. Preparation of 3-(2-oxocyclopentyl)-2-ureidopropanoic acid 3-(2-oxocyclopentyl)-2-ureidopropanoic acid was prepared as described in Example 1, in a similar yield, however with propyl 2-acetamido-3-(2-oxocyclopentyl)-propanoate instead of methyl 2-acetamido-3-(2-oxocyclopentyl) propanoate as starting material.

Example 3

Preparation of
(S)-2-amino-3-(2-oxocyclopentyl)propanoic acid

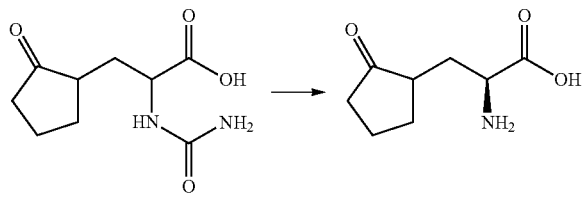

1. Transformation of pKECaroP-hyu1 Construct into *Escherichia coli* RV308
   Thaw *Escherichia coli* RV308 aliquots (200 μl, super competent) on ice
   Add 15 μl LR reaction mix (see above)
   Incubate 30 minutes on ice
   Heat shock 1 minute 42° C.
   Cool cells 2 minutes on ice
   Add 1 mL LB medium (5 g/l NaCl, 5 g/l yeast extract, 10 g/l tryptone)
   Incubate 1 h at 37° C.
   Plate on LB agar plates supplemented with kanamycine (5 g/l NaCl, 5 g/l yeast extract, 10 g/l tryptone, 15 g/l agar, 50 mg/l kanamycine)
   Incubate 24 h at 28° C.
   Isolate single colonies
2. Expression of Hyu Genes in *Escherichia coli* RV308
   Single clones from the transformation (see above) were used to inoculate 5 mL of 2×TY media (10 g/l yeast extract, 16 g/l tryptone, 5 g/l NaCl) supplemented with 0.05 g/l kanamycine and 1 mM $MnCl_2$ or $CoCl_2$, respectively. The culture was incubated at 28° C. and 150 rpm for 24 h and then used for inoculation of 100 mL 2×TY media supplemented with 0.05 g/l kanamycine and 1 mM $MnCl_2$ or $CoCl_2$, respectively. The cultures were again incubated for 24-28 h under conditions previously mentioned and subsequently harvested by centrifugation (20 min, 5000 rpm, 4° C.). The cell pellet was resuspended in 5 mL Tris-HCl (100 mM, pH 7), centrifuged again (20 min, 5000 rpm, 4° C.) and the cells were frozen at −20° C.
3. Bioconversion
   3-(2-oxocyclopentyl)-2-ureidopropanoic acid (15.0 g, 0.07 mol) was suspended in water (90 mL) and the pH was adjusted to 7.3 with a 32% NaOH solution (8.30 g). Then, $MnCl_2$ solution (3.75 mL, 500 mmol/L) was added and 60 g of wet cell slurry obtained according to 'Expression of Hyu genes in *Escherichia coli* RV308' (see above) was added. The reaction was stirred at 28° C. for 20 h and the pH was decreased to 4 or 6, depending on the conditions as used in Example 4, with 85% $H_3PO_4$. The reaction mixture was then centrifuged (12.000 rpm) and the clear liquid was separated from the remaining cell mass.

Example 4

Preparation of (2S,3aS,6aS)-octahydrocyclopenta[b]pyrrole-2-carboxylic acid from (S)-2-amino-3-(2-oxocyclopentyl)propanoic acid From the solution obtained in Example 3 containing (S)-2-amino-3-(2-oxocyclopentyl)propanoic acid, aliquots of 5 mL were taken for hydrogenation experiments. To this solution 0.01-0.1 gram of catalyst was added and the temperature was set at 40-80° C. A hydrogen pressure of 5 or 10 bars was applied and hydrogenation was carried out for 18-20 hours. Multiple experiments were run with variations in catalyst, pH, temperature, hydrogen pressure and duration as outlined in Table 1. After termination of the hydrogenation the diastereomeric excess (d.e.) of the product octahydrocyclopenta[b]pyrrole-2-carboxylic acid was determined by HPLC using an ASTEC CLC-L column (150 mm length, 4.6 mm internal diameter, 5 μm particle size) at 40° C. with 2 mM $CuSO_4$ in water/methanol 95/5 v/v % as eluent. The flow was 1.0 mL/min and UV detection was performed at 254 nm using a Thermo Finnigan Spectra Physics UV 2000 spectrometer. Injection volumes were 6 μL. The retention times for the various isomers were as follows:

$R_t$((2S,3aS,6aS)-octahydrocyclopenta[b]pyrrole-2-carboxylic acid): 12.3 min;

$R_t$((2S,3aR,6aR)-octahydrocyclopenta[b]pyrrole-2-carboxylic acid): 30.3 min.

TABLE 1

Hydrogenation using various catalysts under various conditions

| T (° C.) | pH | P—$H_2$ (bar) | Time (h) | Catalyst | Catalyst amount (g) | Selectivity SSS/SRR (%) |
|---|---|---|---|---|---|---|
| 40 | 4 | 10 | 20 | Pd/C (5%) | 0.1 | 70/30 |
| 60 | 4 | 10 | 20 | Pd/C (5%) | 0.1 | 85/15 |
| 60 | 4 | 10 | 20 | Pd/C (5%) | 0.1 | 68/32 |
| 60 | 4 | 10 | 20 | Pd/C (5%) | 0.03 | — |
| 60 | 4 | 10 | 20 | Pd/C (5%) | 0.03 | — |
| 60 | 6 | 10 | 20 | Pd/C (5%) | 0.1 | 86/14 |
| 60 | 6 | 10 | 20 | Pd/C (5%) | 0.1 | 86/14 |
| 80 | 4 | 10 | 20 | Pd/C (5%) | 0.03 | 95/5 |
| 80 | 4 | 10 | 18 | Pd/C (5%) | 0.1 | 73/27 |
| 80 | 4 | 5 | 18 | Pd/C (5%) | 0.1 | 81/19 |
| 80 | 6 | 10 | 20 | Pd/C (5%) | 0.03 | 96/4 |
| 80 | 6 | 5 | 18 | Pd/C (5%) | 0.1 | 90/10 |
| 80 | 6 | 5 | 18 | Pd/C (5%) | 0.1 | 82/18 |
| 80 | 6 | 5 | 18 | Pd/C (5%) | 0.1 | 88/12 |
| 80 | 6 | 5 | 18 | Pd/C (5%) | 0.1 | 89/11 |
| 80 | 6 | 5 | 18 | Pd/C (5%) | 0.1 | 86/14 |
| 80 | 6 | 5 | 18 | Pd/C (5%) | 0.1 | 77/23 |
| 60 | 4 | 10 | 20 | Pt/C (5%) | 0.1 | 94/6 |
| 60 | 4 | 10 | 20 | Pt/C (5%) | 0.1 | 93/7 |
| 60 | 4 | 10 | 20 | Pt/C (5%) | 0.01 | — |
| 60 | 4 | 10 | 20 | Pt/C (5%) | 0.1 | 93/7 |
| 60 | 4 | 10 | 20 | Pt/C (5%) | 0.03 | — |
| 60 | 4 | 10 | 20 | Pt/C (5%) | 0.03 | 68/32 |
| 60 | 4 | 10 | 18 | Pt/C (5%) | 0.1 | 93/7 |
| 60 | 4 | 5 | 18 | Pt/C (5%) | 0.1 | 94/6 |
| 80 | 4 | 10 | 20 | Pt/C (5%) | 0.03 | 96/4 |
| 80 | 4 | 10 | 20 | Pt/C (5%) | 0.003 | 70/30 |
| 80 | 6 | 5 | 18 | Pt/C (5%) | 0.1 | 92/8 |
| 60 | 6 | 10 | 18 | Raney-cobalt | 0.1 | 99/1 |
| 80 | 4 | 10 | 20 | Raney-cobalt | 0.1 | 70/30 |
| 80 | 6 | 5 | 18 | Raney-cobalt | 0.1 | 99/1 |
| 60 | 6 | 10 | 18 | Raney-nickel | 0.1 | 100/0 |
| 80 | 4 | 10 | 20 | Raney-nickel | 0.1 | 95/5 |
| 80 | 6 | 5 | 18 | Raney-nickel | 0.1 | 100/0 |
| 80 | 6 | 5 | 18 | Raney-nickel | 0.1 | 100/0 |

In a larger scale experiment with Raney-nickel as catalyst, the catalyst was filtered off after conversion on a pad of celite under suction and the product (2S,3aS,6aS)-octahydrocyclopenta[b]pyrrole-2-carboxylic acid was isolated after evaporation of the water layer in vacuo at 80° C. $^1$H NMR: (DMSO-$d_6$, 300 MHz): δ 10.54 (br s, 1H), 8.71 (br s, 1H), 4.22 (dd, 1H), 3.98 (t, 1H), 2.86-2.76 (m, 1H), 2.49-2.42 (m, 1H), 2.00-1.96 (m, 1H), 1.80-1.40 (m, 6H).

Example 5

Preparation of (2S,3aS,6aS)-benzyl octahydrocyclopenta[b]pyrrole-2-carboxylate, 4-toluenesulfonate (1:1) from (2S,3aS,6aS)-octahydrocyclopenta[b]pyrrole-2-carboxylic acid In a round-bottom flask equipped with a Dean-Stark trap, (2S,3aS,6aS)-octahydrocyclo-penta[b]pyrrole-2-carboxylic acid obtained in Example 4 (5.00 g, 32.2 mmol) was suspended in toluene (100 mL) and p-toluenesulphonic acid monohydrate (6.60 g, 34.7 mmol) and benzyl alcohol (15.0 mL, 15.6 g, 144 mmol) were added and the mixture was brought to reflux. The reaction was refluxed for 8 h and then allowed to cool to room temperature. A colorless solid precipitated. Most of the solvent was then removed in vacuo at 65° C. To the residual thick suspension, ethyl ether (200 mL) was added and the solid was collected on a filter (porosity #3) under suction and was further washed with ethyl ether (4×50 mL). The colorless product was allowed to air-dry. Weight 12.1 g, 90% yield.

Example 6

Preparation of N—[(S)-1-(ethoxycarbonyl)-3-phenyl-propyl]L-alanylchloride HCl from N—[(S)-1-(ethoxycarbonyl)-3-phenyl-propyl]-L-alanine N—[(S)-1-(ethoxycarbonyl)-3-phenyl-propyl]L-alanylchloride HCl was synthesized from N—[(S)-1-(ethoxycarbonyl)-3-phenyl-propyl]-L-alanine and $PCl_5$ in $CH_2Cl_2$ at 0±3° C. and precipitated by slow addition of cyclohexane as outlined in US 2006/0079698. Filtration was carried out under an atmosphere of nitrogen.

Example 7

Preparation of (2S,3aS,6aS)-octahydrocyclopenta[b]pyrrole-2-carboxylic acid, 1-[(2S)-2-[[(1S)-1-(ethoxycarbonyl)-3-phenylpropyl]amino]-1-oxopropyl], phenylmethyl ester from (2S,3aS,6aS)-benzyl octahydrocyclopenta[b]pyrrole-2-carboxylate The toluenesulfonate salt prepared in Example 5 (6.00 g, 14.4 mmol) was suspended in $CH_2Cl_2$ (60 mL) and triethylamine (1.46 g, 14.4 mmol) was added at 0° C. The slurry was stirred for 30 min and then imidazole (2.94 g, 43.1 mmol) was added in small portions, followed by N—[(S)-1-(ethoxycarbonyl)-3-phenyl-propyl]L-alanylchloride HCl prepared in Example 6 (5.28 g, 15.8 mmol). The reaction mixture was stirred for 2 h at 0° C. and then allowed to warm to 20° C. within 30 min and stirred at that temperature for 2 h. Water (60 mL) was then added and after vigorous mixing of the phases, the organic layer was separated and the aqueous layer was extracted once more with $CH_2Cl_2$ (60 mL). The combined organic layers were washed with aqueous saturated $NaHCO_3$ (60 mL), treated with charcoal (1 g) and dried over anhydrous $Na_2SO_4$ (5 g). After filtration of the salt and evaporation of the solvent in vacuo at 40° C., the product was obtained as a yellowish oil. This oil was redissolved in methanol (90 mL) and 5% Pd/C (0.50 g) was added and hydrogenation was performed under 2 bar of hydrogen pressure. After approx. 4 h, consumption of hydrogen ceased and the catalyst was filtered off on a pad of celite. Additional methanol was used to wash the celite (20 mL). The organic layer was removed in vacuo at 50° C. The residue was recrystallized from ethyl ether (100 mL) at 0° C. The product ramipril (2) is a colorless solid. Weight 4.56 g, 70% yield.

The invention claimed is:

1. A method for the preparation of a compound of general formula (1),

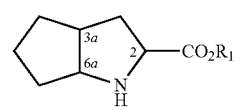

(1)

wherein $R_1$ is hydrogen or a carboxylic acid protecting group, comprising hydrogenation of a compound of general formula (3),

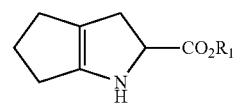

(3)

wherein $R_1$ is as described above, in the presence of a catalyst which comprises cobalt and/or nickel.

2. The method according to claim 1 wherein said compound of general formula (3) is formed in situ from a precursor.

3. The method according to claim 1 wherein in said compound of general formula (1) the configuration at carbon atom 2 is at least 95% S, wherein the configuration at carbon atom 3a is at least 95% S and wherein the configuration at carbon atom 6a is at least 95% S.

4. The method according to claim 1 wherein said catalyst is Raney-cobalt and/or Raney-nickel.

5. A method for the preparation of a compound of general formula (1),

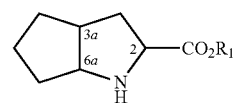

(1)

wherein $R_1$ is alkenyl or substituted alkenyl, alkyl or substituted alkyl, alkylcarbonyl or substituted alkylcarbonyl, aryl or substituted aryl, arylcarbonyl or substituted arylcarbonyl, silyl or substituted silyl, sulfonyl or substituted sulfonyl, comprising hydrogenation of a compound of general formula (3),

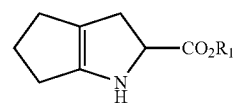

(3)

wherein $R_1$ is as described above, in the presence of a catalyst which comprises cobalt and/or nickel.

* * * * *